(12) United States Patent
Burke et al.

(10) Patent No.: US 11,806,387 B1
(45) Date of Patent: Nov. 7, 2023

(54) PROCESS OF MAKING ABALOPARATIDE

(71) Applicant: Radius Health, Inc., Boston, MA (US)

(72) Inventors: Matt Burke, Wayne, PA (US); Silvio Campagna, Lehigh Acres, FL (US)

(73) Assignee: Radius Health, Inc., Boston, MA (US)

(*) Notice: Subject to any disclaimer, the term of this patent is extended or adjusted under 35 U.S.C. 154(b) by 0 days.

(21) Appl. No.: 18/320,544

(22) Filed: May 19, 2023

Related U.S. Application Data

(60) Provisional application No. 63/344,375, filed on May 20, 2022.

(51) Int. Cl.
| | |
|---|---|
| *C07K 1/06* | (2006.01) |
| *C07K 14/635* | (2006.01) |
| *A61K 38/29* | (2006.01) |
| *C07K 1/04* | (2006.01) |
| *C07K 1/08* | (2006.01) |

(52) U.S. Cl.
CPC .............. *A61K 38/29* (2013.01); *C07K 1/066* (2013.01); *C07K 14/635* (2013.01); *C07K 1/04* (2013.01); *C07K 1/06* (2013.01); *C07K 1/084* (2013.01)

(58) Field of Classification Search
CPC .......... A61K 38/29; C07K 1/06; C07K 1/066; C07K 14/635
See application file for complete search history.

(56) References Cited

U.S. PATENT DOCUMENTS

| | | | |
|---|---|---|---|
| 5,969,095 A | 10/1999 | Dong | |
| 2002/0022596 A1* | 2/2002 | Al-Obeidi | C07K 5/0202 562/443 |
| 2017/0173107 A1* | 6/2017 | Lambris | C07K 7/08 |
| 2021/0230216 A1 | 7/2021 | Yin et al. | |

FOREIGN PATENT DOCUMENTS

| | | |
|---|---|---|
| CN | 106146648 A | 11/2016 |
| WO | 2020/202182 A1 | 10/2020 |
| WO | 2020/208650 A1 | 10/2020 |

* cited by examiner

*Primary Examiner* — Jeffrey E. Russel
(74) *Attorney, Agent, or Firm* — Womble Bond Dickinson (US) LLP

(57) ABSTRACT

Disclosed herein is an improved process for preparing abaloparatide. The process generally utilizes solid phase peptide synthesis employing an Fmoc-protection scheme. Incorporating a systematic recoupling step of a glutamine residue ($Gln^{16}$) has been found to minimize the formation of an undesirable des-$Gln^{16}$ abaloparatide impurity, which is often obtained in significant quantities in the conventional process.

28 Claims, 6 Drawing Sheets

Specification includes a Sequence Listing.

PROCESS OF MAKING ABALOPARATIDE

PRIORITY CLAIM

This application claims the benefit of U.S. Provisional Application No. 63/344,375, filed May 20, 2022, the entire content of which is incorporated herein by reference in its entirety, including drawings.

SEQUENCE LISTING

The instant application contains a Sequence Listing which has been submitted electronically in XML format and is hereby incorporated by reference in its entirety. Said CRF copy, created on Aug. 15, 2023, is named SL1240.xml and is 7,996 bytes in size.

TECHNICAL FIELD

The present disclosure relates to an improved process for the preparation of abaloparatide.

BACKGROUND

Abaloparatide is a synthetic 34 amino acid peptide analog of human parathyroid hormone-related peptide, hPTHrP(1-34) having 76% homology to hPTHrP(1-34) and 41% homology to human parathyroid hormone (hPTH(1-34)). Abaloparatide has a molecular formula of $C_{174}H_{300}N_{56}O_{49}$, a molecular weight of 3961 daltons, and the amino acid sequence:

Ala$^1$-Val-Ser-Glu-His$^5$-Gln-Leu-Leu-His-Asp$^{10}$-Lys-Gly-Lys-Ser-Ile$^{15}$-Gln-Asp-Leu-Arg-Arg$^{20}$-Arg-Glu-Leu-Leu-Glu$^{25}$-Lys-Leu-Leu-Aib-Lys$^{30}$-Leu-His-Thr-Ala$^{34}$-NH$_2$ (SEQ ID NO: 1).

The structure and preparation of abaloparatide has been previously disclosed in, for example, U.S. Pat. No. 5,969,095, which is hereby incorporated by reference. A product containing abaloparatide, formulated for subcutaneous injection and used for treatment of osteoporosis in postmenopausal women, is available under the brand name TYMLOS, marketed by Radius Health Inc.

The conventional preparative method for synthesis of abaloparatide can yield substantial amounts of deletion impurities, in which particular amino acids are missing from the growing amino acid sequence. While such impurities can be removed during downstream processing, this directly impacts product yield and cost of goods. Large batch-to-batch yield variability has been observed resulting from the formation of such deletion products. Accordingly, it would be desirable to provide a process which reduces or avoids the formation of deletion impurities.

SUMMARY OF THE INVENTION

The preparation of abaloparatide is generally performed using solid phase synthesis methodology in which a series of sequential coupling and deprotection reactions of protected amino acids is performed, followed by global deprotection and cleavage from the solid phase resin. An in-process test is typically used after each coupling reaction to ensure that each amino acid has been successfully added. The coupling of certain amino acids is relatively more problematic, and failure to achieve quantitative coupling leads to deletion impurities (i.e., peptides missing a particular amino acid residue). For example, the addition of glutamine residue 16 (Gln$^{16}$; added as Fmoc-Gln(Trt)) to the growing N-terminal peptide chain has been identified as particularly problematic according to the present disclosure. Compounding the issue, the in-process test (Kaiser test) used to confirm complete incorporation has surprisingly been demonstrated to provide inaccurate results according to the present disclosure.

Without wishing to be bound by theory, it is believed that electrostatic and/or steric hindrance at the reactive site of coupling may provide the false positive result with respect to complete Gln$^{16}$ incorporation. Relying on the inaccurate Kaiser test has resulted in recent batches in which the Gln$^{16}$ deletion impurity comprises up to 49% by weight of the crude abaloparatide product (see, for example FIG. 2, which provides a graphical summary of recent preparation campaigns). The data in FIG. 2 demonstrate that the Gln$^{16}$ deletion product was observed in 43% of the previous batches, despite negative Kaiser tests in each instance. While subsequent purification steps adequately remove the deletion impurity in the conventional production process, the result is low and inconsistent batch yield and significant waste.

According to the present disclosure, it has been discovered that routinely repeating the Gln$^{16}$ coupling reaction, without regard to the outcome of the Kaiser test, results in a more robust, higher yielding process in which the Gln$^{16}$ deletion impurity has been dramatically reduced (e.g., to levels of less than 1%).

Thus, in one aspect is provided a process for the preparation of abaloparatide comprising:

a) providing a peptide bound to a solid resin and having an initial N-terminus, wherein said bound peptide is NH$_2$-Asp(OtBu)-Leu-Arg(Pbf)-Arg$^{20}$-(Pbf)-Arg(Pbf)-Glu(OtBu)-Leu-Leu-Glu$^{25}$(OtBuLys(Boc)-Leu-Leu-Aib-Lys$^{30}$-(Boc)-Leu-His(Trt)-Thr(tBu)-Ala$^{34}$-Rink Amide MBHA resin (SEQ ID NO:2);

b) coupling a carboxyl terminus of Fmoc-(Trt)Gln$^{16}$-OH to the initial N-terminus of the bound peptide in the presence of a coupling reagent;

c) repeating step b) to ensure complete incorporation of Fmoc-(Trt)Gln$^{16}$;

d) selectively cleaving the Fmoc group with a solution comprising an amine base to provide a peptide bound to a solid resin and having a new N-terminus.

In some embodiments, the coupling reagent comprises PyBOP, HOBt, DIC, and DIEA.

In some embodiments, steps b) and e) are performed using 1.5 molar equivalents of Fmoc-(Trt)Gln$^{16}$-OH, relative to the bound peptide.

In some embodiments, the amine base is piperidine. In some embodiments, the piperidine is present as an approximately 20% solution by weight in DMF.

In some embodiments, the process further comprises:

e) coupling a carboxyl terminus of Fmoc-Ile$^{15}$-OH to the new N-terminus in the presence of a coupling reagent;

f) selectively cleaving the Fmoc group with a solution comprising an amine base to provide a peptide bound to the solid resin and having a new N-terminus; and g) repeating steps e) and f), wherein each step e) is performed, in sequential order, substituting the Fmoc-Ile$^{15}$-OH with the following Fmoc-protected amino acids: Ser(tBu)$^{14}$-OH, Lys(Boc)$^{13}$-OH, Gly$^{12}$-OH, Lys(Boc)$^{11}$-OH, Asp$^{10}$(OtBu)-OH, His(Trt)$^9$-OH, Leu$^8$-OH, Leu$^7$-OH, Gln(Trt)$^6$-OH, His$^5$(Trt)-OH, Glu(OtBu)$^4$-OH, Ser(tBu)$^3$-OH, Val$^2$-OH, and Ala$^1$-OH, to form a thirty-four amino acid peptide sequence bound to the solid resin.

In some embodiments, the coupling reagent comprises PyBOP, HOBt, DIC, and DIEA.

In some embodiments, each coupling step e) is performed using 1.5 molar equivalents of the Fmoc-amino acid, relative to the bound peptide.

In some embodiments, the amine base is piperidine. In some embodiments, the piperidine is present as an approximately 20% solution by weight in DMF.

In some embodiments, the process further comprises:
h) performing a Kaiser and/or Chloranil test after each step e) but before each step f) to confirm complete incorporation of each Fmoc-protected amino acid; and
i) performing a recoupling reaction if a positive Kaiser or Chloranil test result is obtained.

In some embodiments, performing the recoupling reaction comprises performing a coupling reaction with the Fmoc-protected amino acid one or more additional times, using from 0.15 to 1.5 molar equivalents of the respective Fmoc-amino acid relative to the bound peptide, repeating said coupling until a negative Kaiser or Chloranil test result is obtained.

In some embodiments, the process further comprises:
j) treating the thirty-four amino acid peptide sequence bound to the solid resin with a solution comprising trifluoroacetic acid to provide crude abaloparatide.

In some embodiments, the crude abaloparatide contains less than about 1% of des-Gln$^{16}$-abaloparatide by weight, based on the total weight of the crude abaloparatide. In some embodiments, the crude abaloparatide contains less than about 0.5% des-Gln$^{16}$-abaloparatide by weight, based on the total weight of the crude abaloparatide. In some embodiments, the crude abaloparatide contains less than about 0.3% des-Gln$^{16}$-abaloparatide by weight, based on the total weight of the crude abaloparatide.

In some embodiments, providing the peptide bound to the solid resin comprises:
k) anchoring Fmoc-protected alanine (Fmoc-Ala$^{34}$-OH) to Rink amide 4-methylbenzhydrylamine (MBHA) resin;
l) capping the resin obtained in step k) by acetylation;
m) selectively cleaving the Fmoc group with a solution comprising an amine base to provide an N-terminus;
n) coupling a carboxyl terminus of Fmoc-Thr(tBu)$^{33}$-OH to the N-terminus in the presence of a coupling reagent;
o) performing a Kaiser and/or Chloranil test after each step n) to confirm complete incorporation of each Fmoc-protected amino acid, and performing a recoupling reaction if a positive Kaiser or Chloranil test result is obtained;
p) selectively cleaving the Fmoc group with a solution comprising an amine base to provide an N-terminus;
q) repeating steps n) through p) sequentially, replacing the Fmoc-Thr(tBu)$^{33}$-OH with the following series of Fmoc-protected amino acids: His(Trt)$^{32}$-OH, Leu$^{31}$-OH, (Boc)Lys$^{30}$-OH, Aib$^{29}$-OH, Leu$^{28}$-OH, Leu$^{27}$-OH, (Boc)Lys$^{26}$-OH, (OtBu)Glu$^{23}$-OH, Leu$^{24}$-OH, Leu$^{23}$-OH, (OtBu)Glu$^{22}$-OH, (Pbf)Arg$^{21}$-OH, (Pbf)-Arg$^{20}$-OH, (Pbf)Arg$^{19}$-OH, Leu$^{18}$-OH, and (OtBu)Asp$^{17}$-OH.

In some embodiments, the coupling reagent comprises PyBOP, HOBt, DIC, and DIEA.

In some embodiments, the amine base is piperidine. In some embodiments, the piperidine is present as an approximately 20% solution by volume in DMF.

In some embodiments, each coupling step n) is performed using 1.5 molar equivalents of Fmoc-amino acid, relative to the bound peptide.

In some embodiments, performing the recoupling reaction comprises performing a coupling reaction with the Fmoc-protected amino acid one or more additional times, using from 0.15 to 1.5 molar equivalents of the respective Fmoc-amino acid relative to the bound peptide, and repeating said coupling until a negative Kaiser or Chloranil test result is obtained.

In another aspect is provided a process for the preparation of abaloparatide comprising:
a) anchoring Fmoc-protected alanine (Fmoc-Ala$^{34}$-OH) to Rink amide 4-methylbenzhydrylamine (MBHA) resin;
b) capping the resin obtained in step a) by acetylation;
c) selectively cleaving the Fmoc group with a solution comprising piperidine to provide an N-terminus;
d) coupling a carboxyl terminus of Fmoc-Thr(tBu)$^{33}$-OH to the N-terminus in the presence of a coupling reagent comprising benzotriazol-1-yloxytripyrrolidinophosphonium hexafluorophosphate (PyBOP), 1-Hydroxybenzotriazole (HOBt), N,N'-diisopropylcarbodiimide (DIC), and diisopropylethylamine (DIEA), performing a Kaiser and/or Chloranil test after each step d) to confirm complete incorporation of each Fmoc-protected amino acid, and repeating said step d) if a positive Kaiser or Chloranil test result is obtained;
e) selectively cleaving the Fmoc group with a solution comprising piperidine to provide an N-terminus;
f) repeating steps d) and e) sequentially, replacing the Fmoc-Thr(tBu)$^{33}$-OH with the following series of Fmoc-protected amino acids: His(Trt)$^{32}$-OH, Leu$^{31}$-OH, (Boc)Lys$^{30}$-OH, Aib$^{29}$-OH, Leu$^{28}$-OH, Leu$^{27}$-OH, (Boc)Lys$^{26}$-OH, (OtBu)Glu$^{23}$-OH, Leu$^{24}$-OH, Leu$^{23}$-OH, (OtBu)Glu$^{22}$-OH, (Pbf)Arg$^{21}$-OH, (Pbf)-Arg$^{20}$-OH, (Pbf)Arg$^{19}$-OH, Leu$^{18}$-OH, and (OtBu)Asp$^{17}$-OH, and performing a Kaiser and/or Chloranil test after each step d) before each step e) to confirm complete incorporation of each Fmoc-protected amino acid, and repeating said step d) if a positive Kaiser or Chloranil test result is obtained;
g) coupling a carboxyl terminus of Fmoc-(Trt)Gln$^{16}$-OH to the N-terminus in the presence of a coupling reagent comprising PyBOP, HOBt, DIC, and DIEA;
h) repeating step g) to ensure complete incorporation of Fmoc-(Trt)Gln$^{16}$;
i) selectively cleaving the Fmoc group with a solution comprising piperidine to provide an N-terminus;
j) coupling a carboxyl terminus of Fmoc-Ile$^{15}$-OH to the N-terminus in the presence of a coupling reagent comprising PyBOP, HOBt, DIC, and DIEA;
k) selectively cleaving the Fmoc group with a solution comprising piperidine to provide an N-terminus;
l) repeating steps j) and k) sequentially, replacing Fmoc-Ile$^{15}$-OH with the following series of Fmoc-protected amino acids: Ser (tBu)$^{14}$-OH, Lys (Boc)$^{13}$-OH, Gly$^{12}$-OH, Lys(Boc)$^{11}$-OH, Asp(OtBu)$^{10}$-OH, His(Trt)$^{9}$-OH, Leu$^{8}$-OH, Leu$^{7}$-OH, Gln(Trt)$^{6}$-OH, His (Trt)$^{5}$-OH, Glu (OtBu)$^{4}$-OH, Ser(tBu)$^{3}$-OH, Val$^{2}$-OH, and Ala$^{1}$-OH;
m) performing a Kaiser and/or Chloranil test after each step j) before each step k) to confirm complete incorporation of each Fmoc-protected amino acid, and repeating said step j) if a positive Kaiser or Chloranil test result is obtained; and
n) treating the resulting anchored, protected abaloparatide with a solution comprising trifluoroacetic acid to provide crude abaloparatide.

In some embodiments, each initial coupling reaction is performed using 1.5 molar equivalents of the respective Fmoc-amino acid relative to the bound peptide; and any repeated couplings performed following a positive Kaiser or Chloranil test are performed using from 0.15 to 2 molar equivalents of the respective Fmoc-amino acid.

In some embodiments, in step f), the coupling of Fmoc-protected $Aib^{29}$-OH is repeated once prior to cleavage of the Fmoc group, without regard to the Kaiser or Chloranil test, the repeated coupling using 1.5 equivalents of the Fmoc-protected $Aib^{29}$-OH.

In some embodiments, in step f), the coupling of the Fmoc-protected $Leu^{28}$-OH is repeated once prior to cleavage of the Fmoc group, without regard to the Kaiser or Chloranil test, the repeated coupling using 1.5 equivalents of the Fmoc-protected $Leu^{28}$-OH.

In some embodiments, the piperidine is present as an approximately 20% solution by volume in DMF.

In some embodiments, the obtained crude abaloparatide contains less than about 1% of des-$Gln^{16}$-abaloparatide by weight, based on the total weight of the crude abaloparatide. In some embodiments, the obtained crude abaloparatide contains less than about 0.5% des-$Gln^{16}$-abaloparatide by weight, based on the total weight of the crude abaloparatide. In some embodiments, the obtained crude abaloparatide contains less than about 0.3% des-$Gln^{16}$-abaloparatide by weight, based on the total weight of the crude abaloparatide.

DETAILED DESCRIPTION OF THE INVENTION

Figure 1:
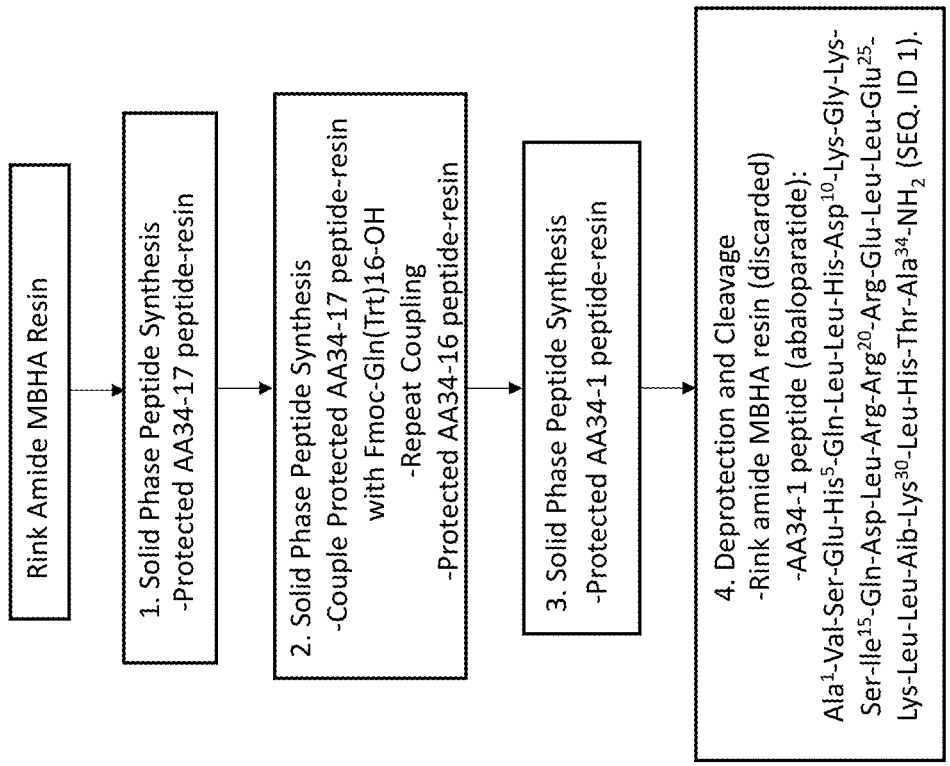
FIG. 1 is a flow chart depicting a generalized synthesis scheme according to a non-limiting embodiment of the disclosed method.
Figure 2:
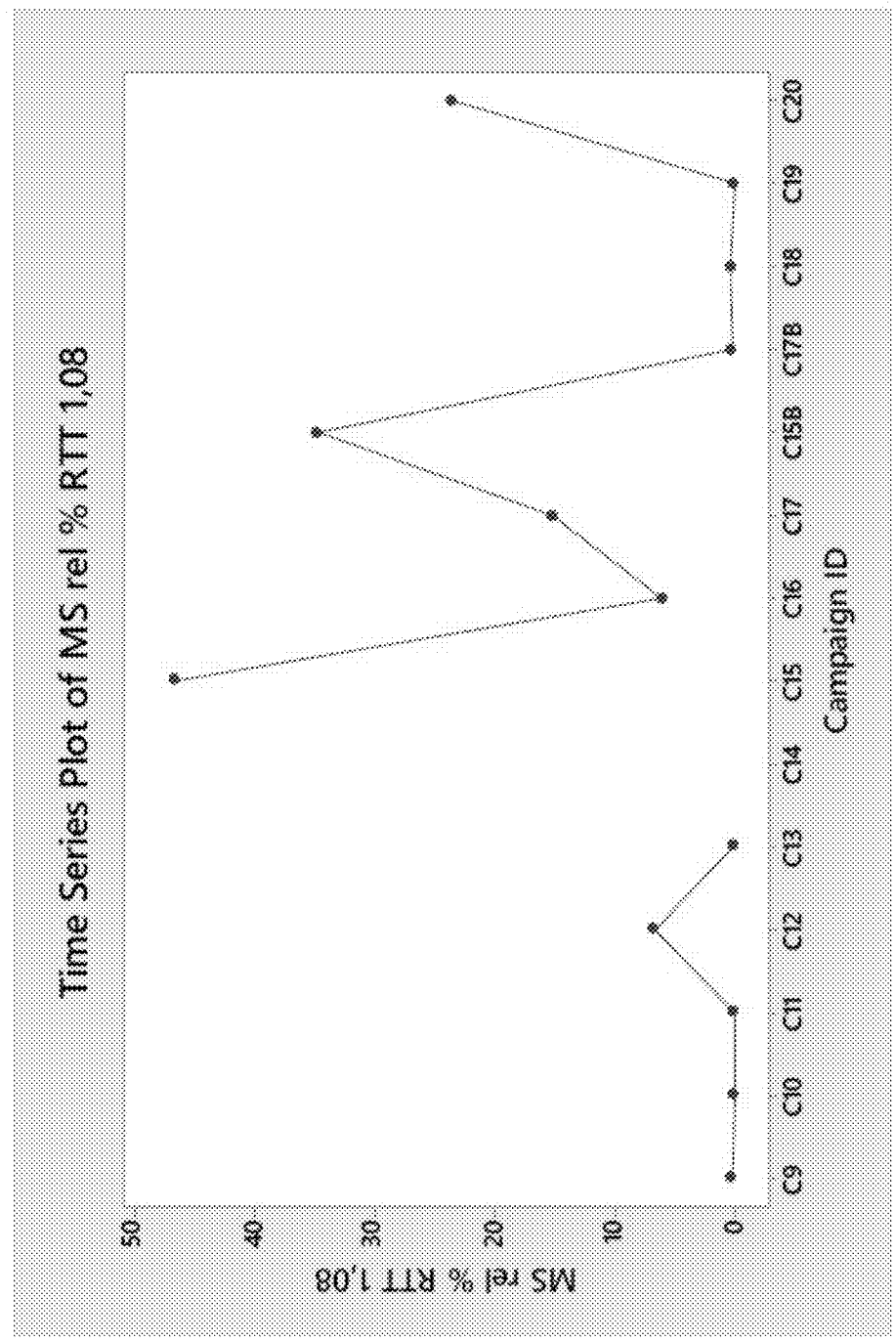
FIG. 2 is a graph summarizing percent by weight of Gln16 deletion product in recent batches of abaloparatide prepared by the conventional method.

The present disclosure provides a process for preparing abaloparatide. The process generally comprises sequentially coupling and deprotecting a series of Fmoc-protected amino acids utilizing solid phase peptide synthesis (SPPS) techniques, followed by cleavage of the desired peptide from the solid phase support. The process relies on the surprising discovery that 1) the conventionally employed Kaiser test is often inaccurate, failing to detect the failure of complete introduction of Gln16 into the growing peptide chain; and 2) a systematic recoupling of Gln16 without regard to the Kaiser test result provides abaloparatide with greatly reduced quantities of the undesired Gln16 deletion product.

Accordingly, disclosed herein is a process for the preparation of abaloparatide. The process generally comprises providing a peptide bound to a solid resin; coupling Fmoc-(Trt)$Gln^{16}$-OH to the bound peptide, repeating the coupling to ensure complete incorporation of Fmoc-(Trt)$Gln^{16}$, and selectively cleaving the Fmoc group. The process and each of the individual steps is described further herein below.

Definitions

While the terms used herein are believed to be well understood by one of ordinary skill in the art, definitions are set forth herein to facilitate explanation of the presently-disclosed subject matter.

The articles "a" and "an" are used herein to refer to one or to more than one (i.e., to at least one) of the grammatical object of the article. The term "about" used throughout this specification is used to describe and account for small fluctuations. For example, the term "about" can refer to less than or equal to ±5%, such as less than or equal to ±2%, less than or equal to ±1%, less than or equal to ±0.5%, less than or equal to ±0.2%, less than or equal to ±0.1% or less than or equal to ±0.05%. All numeric values herein are modified by the term "about," whether or not explicitly indicated. A value modified by the term "about" of course includes the specific value. For instance, "about 5.0" must include 5.0.

As used herein, the term "solid-phase peptide synthesis (SPPS)" refers to a process in which a peptide unit, anchored by its C-terminus to a resin, is assembled by the successive addition of protected amino acids constituting the sequence of said peptide.

As used herein, the term "Kaiser test" refers to a test commonly used to detect the presence of a primary amine (—$NH_2$) during SPPS chemistry. Specifically, the Kaiser test uses a ninhydrin-based reagent solution to provide a colorimetric indication of the completion of an amino acid coupling reaction. A colorless result or a faint blue color ("negative") indicates complete coupling has occurred (i.e., no detectable primary amine is present), while a darker blue ("positive") indicates an incomplete and/or failed coupling (i.e., a detectable quantity of primary amine is present). The Kaiser test is not suitable for indication of the presence of secondary amines, and is generally replaced in such instances with the Chloranil test.

As used herein, the term "Chloranil test" refers to a test commonly used to detect the presence of a secondary amine (—RNH) during SPPS chemistry. Specifically, the Chloranil test uses a p-chloranil and acetaldehyde based reagent to provide a colorimetric indication of the completion of an amino acid coupling reaction. A colorless result ("negative") indicates complete coupling has occurred (i.e., no detectable secondary amine is present), while a dark blue color ("positive") indicates an incomplete and/or failed coupling (i.e., a detectable quantity of secondary amine is present).

Abbreviations

The following is a list of abbreviations and their meanings
Aib: 2-Aminoisobutyric acid
Ala: Alanine
Arg: Arginine
Asp: Aspartic acid
Boc: Di-tert-butyl-dicarbonate
tBu: tert-butyl
DCM: dichloromethane
DIC: N,N'-diisopropylcarbodiimide
DIEA: Diisopropylethylamine
DMF: N,N'-Dimethylformamide
EDT: ethanedithiol
Fmoc: 9-fluorenylmethoxycarbonyl
Gln: Glutamine
Glu: Glutamic acid
Gly: Glycine
HBTU: 2-(1H-Benzotriazol-1-yl)-N,N,N',N'-tetramethyl-uronium hexafluorophosphate His: Histidine
HOBt: N-hydroxybenzotriazole
Ile: Isoleucine
Leu: Leucine
Lys: Lysine
MBHA: methylbenzhydrylamine
MTBE: Methyl tert-butyl ether
NMP: N-Methyl-2-pyrrolidone
Pbf: pentmethyldihydrobenzofuransulfonyl
Ser: Serine
TFA: trifluoroacetic acid
Thr: Threonine
TIPS: triisopropylsilane
Trt: Trityl
Tyr: Tyrosine
Val: Valine Process for the Preparation of Abaloparatide The process for the preparation of abaloparatide as disclosed herein generally comprises:
  a) providing a peptide bound to a solid resin and having an initial N-terminus, wherein said bound peptide is NH$_2$-Asp(OtBu)-Leu-Arg(Pbf)-Arg$^{20}$-(Pbf)-Arg(Pbf)-Glu(OtBu)-Leu-Leu-Glu$^{25}$(OtBu)-Lys(Boc)-Leu-Leu-Aib-Lysm-(Boc)-Leu-His(Trt)-Thr(tBu)-Ala$^{34}$-Rink Amide MBHA resin (SEQ ID NO:2).
  b) coupling a carboxyl terminus of Fmoc-(Trt)Gln$^{16}$-OH to the initial N-terminus of the bound peptide in the presence of a coupling reagent comprising PyBOP, HOBt, DIC, and DIEA;
  c) repeating step b) to ensure complete incorporation of Fmoc-(Trt)Gln$^{16}$; and
  d) selectively cleaving the Fmoc group with a solution comprising an amine base to provide a peptide bound to a solid resin and having a new N-terminus.

The coupling is generally performed with a suitable coupling reagent including, but not limited to, one or more of: hydroxybenzotriazole (HOBt), N, N'-diisopropylcarbodiimide (DIC), O-(Benzotriazol-1-yl)-N,N,N',N'-tetramethyluronium tetrafluoroborate (TBTU), N,N,N,N-Tetramethyl-O-(1H-benzotriazol-1-yl)uronium hexafluorophosphate (HBTU), 1,3-dicyclohexylcarbodiimide (DCC), 1-(dimethylaminopropyl)-3-ethylcarbodiimide hydrochloride (EDC HCl), benzotriazol-1-yl-oxy-tris(dimethyl-amino)-phosphonium hexafluorophosphate (BOP), N,N-bis-(2-oxo-3-oxazolidinyl)phosphonic dichloride (BOP-Cl), benzotriazol-1-yloxytri(pyrrolidino)phosphonium hexafluorophosphate (PyBOP), bromotri(pyrrolidino) phosphonium hexafluorophosphate (PyBrOP), chlorotri (pyrrolidino)phosphonium hexafluorophosphate (PyClOP), ethyl-2-cyano-2-(hydroxyimino) acetate (Oxyma Pure), O-(6-Chloro-1-hydrocibenzotriazol-1-yl)-1,1,3,3-tetramethyluronium tetrafluoroborate (TCTU), 2,4,5-norbornen-2,3-dicarboximido)-1,1,3,3-tetramethyluronium tetrafluoroborate (TNTU), 2-succinimido-1,1,3,3-tetramethyluronium tetrafluoro borate (TSTU), 1-Cyano-2-ethoxy-2-oxoethylidenaminooxy)dimethylamino-morpholino-carbenium hexafluorophosphate (COMU), and 3-(diethoxyphosphoryloxy)-1,2,3-benzotriazin-4(3H)-one (DEPBT). In some embodiments, the coupling reagent comprises benzotriazol-1-yloxytripyrrolidinophosphonium hexafluorophosphate (PyBOP), 1-Hydroxybenzotriazole (HOBt), and N,N'-diisopropylcarbodiimide (DIC). In some embodiments, the coupling reagent comprises PyBOP, HOBt, and DIC.

The reaction occurs under neutral or mildly basic conditions; accordingly, an amine base is generally present in the coupling reagent mixture. In some embodiments, the amine base is diisopropylethylamine (DIEA). In some embodiments, sufficient DIEA is added to provide a pH of 7.

The coupling reaction generally takes place in a solvent. Suitable solvents include DMF, DCM, THF, NMP, DMAC, dichloroethane, 1,4-dioxane, 2-methyltetrahydrofuran, ethyl acetate, acetonitrile, acetone, and mixtures of any thereof. In some embodiments, the solvent is DMF.

The quantity of Fmoc-amino acid (e.g., Fmoc-(Trt)Gln$^{16}$-OH) may vary. Generally, the quantity will be stoichiometric (1:1) or greater (e.g., from about 1.05 to about 2 equivalents) relative to the molar amount of bound peptide. In some embodiments, the coupling reaction is performed using 1.5 equivalents of Fmoc-(Trt)Gln$^{16}$-OH.

As described herein above, in the conventional process, a Kaiser test is generally utilized after each amino acid coupling to determine if amino acid residue incorporation is complete prior to deprotecting the Fmoc group and proceeding with sequential coupling reactions. According to the present disclosure, it has been surprisingly found that in certain instances, the Kaiser test is unreliable or insensitive, and provides a false negative result. Without wishing to be bound by theory, it is believed that one or more of steric hindrance, electrostatic interactions, or peptide aggregation prevents reaction of the Kaiser reagent with the primary amine. In instances of a false negative result, proceeding with the subsequent deprotection and coupling reaction will lead to a deletion impurity. Such deletion impurities, while removed during final purification, lower the overall yield of the peptide (i.e., abaloparatide). It has been discovered according to the present disclosure that a Kaiser test performed following coupling of trityl-protected glutamine residue 16 (Gln$^{16}$) with the growing peptide chain is particularly prone to false negative results.

In previous abaloparatide synthesis campaigns, relying on the Kaiser test result, as much as 49% of the total peptide material produced was the Gln$^{16}$ deletion product, i.e., a 33-amino acid analog of abaloparatide in which glutamine residue 16 is missing. This has been observed in 43% of the recent historical production campaigns. To overcome the problem, in the present disclosure, the Kaiser test has been eliminated following the Gln$^{16}$ coupling step. Instead, a systematic recoupling is performed in which the coupling reaction with Fmoc-Gln(Trt)$^{16}$-OH is repeated one or more times. In some embodiments, the coupling is repeated once.

The amount of Fmoc-Gln(Trt)$^{16}$-OH utilized may vary, for example, from about 0.15 to about 2.0 molar equivalents relative to the bound peptide. In some embodiments, the repeated coupling is performed with 1.5 molar equivalents of Fmoc-Gln(Trt)$^{16}$-OH. In some embodiments, the coupling reagent is 2×1.5 equivalents of DIC, 1.5 equivalents of HOBT, 0.25 equivalents of PyBOP, and DIPEA added to provide a pH of 7.

In some embodiments, selectively cleaving the Fmoc group comprises removing the Fmoc group with an amine base. Suitable amine bases include piperidine, piperazine, N-methyl morpholine, diethylamine, triethylamine, 1,8-Diazabicyclo[5.4.0]undec-7-ene (DBU), and mixtures thereof. In some embodiments, the amine base is piperidine.

The removal is conducted in a solvent. In some embodiments, the solvent is N,N-dimethylformamide (DMF), methylene chloride, tetrahydrofuran, N-methyl pyrrolidine, or mixtures thereof. In some embodiments, the amine base is piperidine, present as a 20% solution by volume in DMF.

In some embodiments, the process further comprises:
  e) coupling a carboxyl terminus of Fmoc-Ile$^{15}$-OH to the new N-terminus in the presence of a coupling reagent;

f) selectively cleaving the Fmoc group with a solution comprising an amine base to provide a peptide bound to the solid resin and having a new N-terminus; and
g) repeating steps e) and f), wherein each step e) is performed, in sequential order, substituting the Fmoc-Ile$^{15}$-OH with the following Fmoc-protected amino acids: Ser(tBu)$^4$-OH, Lys(Boc)$^{13}$-OH, Gly$^{12}$-OH, Lys(Boc)$^{13}$-OH, Asp$^{10}$(OtBu)-OH, His(Trt)$^9$-OH, Leu$^8$-OH, Leu$^7$-OH, Gln(Trt)$^6$-OH, His$^5$(Trt)-OH, Glu(OtBu)$^4$-OH, Ser(tBu)$^3$-OH, Val$^2$-OH, and Ala$^1$-OH, to form a thirty-four amino acid peptide sequence bound to the solid resin.

In some embodiments, the coupling reagent comprises PyBOP, HOBt, DIC, and DIEA.

In some embodiments, each coupling step e) is performed using 1.5 equivalents of the Fmoc-amino acid.

In some embodiments, the amine base is piperidine, present as a 20% solution by volume in DMF.

In some embodiments, the process further comprises:
h) performing a Kaiser and/or Chloranil test after each step e) but before each step f) to confirm complete incorporation of each Fmoc-protected amino acid; and
i) performing a recoupling reaction if a positive Kaiser or Chloranil test result is obtained.

In some embodiments, performing a recoupling reaction comprises performing a coupling reaction with the Fmoc-protected amino acid one or more additional times. For example, if following a given coupling reaction, a positive Kaiser test is obtained, the coupling reaction is repeated using various quantities of Fmoc-protected amino acid until a negative Kaiser or Chloranil test result is obtained. The quantity of Fmoc-protected amino acid relative to the bound peptide may vary from, for example, about 0.15 to about 2 molar equivalents, depending on the degree of positive result obtained in the Kaiser test. In some embodiments, the quantity of Fmoc-protected amino acid is about 0.15, about 0.25, about 0.5, about 1.0, or about 1.5 equivalents.

It has further been discovered according to the present disclosure that introduction of amino acid 18 (Leucine; introduced as FMOC-Leu-OH) is difficult, and the Kaiser test can potentially result in a false positive. Specifically, it was observed during several synthetic campaigns that a lightly positive Kaiser result was obtained for amino acid 18 introduction, although the reaction was complete as determined by HPLC analysis (absence of an AA18 deletion impurity). The Kaiser test did not result in a negative result, and a lightly positive test result was subsequently obtained after performing recoupling. It was further discovered that when the Kaiser test is repeated after recoupling, the reaction may be deemed complete if two subsequent slightly positive results are comparable, i.e., a Kaiser test result at t=60 mins (T2) is consistent with a t=90 min (T3) result. Accordingly, in some embodiments, the process comprises utilizing a tiered approach to the Kaiser test for introduction of amino acid 18 (AA18). In some embodiments, the process further comprises using the tiered Kaiser Test approach provided in Table 1.

TABLE 1

| Amino Acid 18 Kaiser Test Approach | | |
|---|---|---|
| Kaiser Test | Result | Next Step |
| T1 (t = 30 mins) | Negative | Reaction complete-Go to Washing step |
| | Lightly positive | Partial completion-perform recoupling and repeat Kaiser test at t = 60 mins |
| | Positive | Incomplete reaction-perform recoupling and repeat Kaiser test at t = 60 mins |
| T2 (t = 60 mins) | Negative | Reaction complete-Go to Washing step |
| | Lightly positive | Repeat Kaiser test at t = 90 mins |
| | Positive | Incomplete reaction. Repeat Kaiser test at t = 90 mins. |
| T3 (t = 90 mins) | Negative | Reaction complete-Go to Washing step |
| | Lightly positive | Result (color) same as t = 60 mins then reaction considered as complete-Go to Washing step. If T2 and T3 are not comparable, wait for another 30 mins and repeat Kaiser Test |
| | Positive | Incomplete reaction |

Following complete construction of the 34-amino acid peptide bound to the Rink amide resin, the peptide is generally cleaved from the resin under acidic conditions. Such acidic conditions generally also globally deprotect all remaining acid-labile protecting groups (e.g., BOC, tBu, Trt and Pbf). The cleavage of the peptide from the resin involves treating the protected peptide, anchored to the resin, with an acid in the presence of at least one scavenger. A particularly suitable acid is TFA. Suitable scavengers include TIPS, phenol, thioanisole, water, ethanedithiol (EDT), and mixtures thereof. In some embodiments, the cleavage solution is TFA/H$_2$O/TIPS/EDT in a volume ratio of 92.5/2.5/2.5/2.5.

Providing the Bound Peptide

Methods disclosed herein comprise providing a peptide bound to a solid resin and having an initial N-terminus, wherein said bound peptide is NH$_2$-Asp(OtBu)-Leu-Arg(Pb)-Arg$^{20}$-(Pbf)-Arg(Pbf)-Glu(OtBu)-Leu-Leu-Glu$^{23}$(OtBu)-Lys(Boc)-Leu-Leu-Aib-Lys$^{30}$-(Boc)-Leu-His(Trt)-Thr(tBu)-Ala$^{34}$-Rink Amide MBHA resin (SEQ ID NO:2). In some embodiments, providing the bound peptide comprises:
k) anchoring Fmoc-protected alanine (Fmoc-Ala$^{34}$-OH) to Rink amide 4-methylbenzhydrylamine (MBHA) resin;
l) capping the resin obtained in step k) by acetylation;
m) selectively cleaving the Fmoc group with a solution comprising an amine base to provide an N-terminus;
n) coupling a carboxyl terminus of Fmoc-Thr(tBu)$^{33}$-OH to the N-terminus in the presence of a coupling reagent;
o) performing a Kaiser and/or Chloranil test after each step n) to confirm complete incorporation of each Fmoc-protected amino acid, and performing a recoupling reaction if a positive Kaiser or Chloranil test result is obtained;
p) selectively cleaving the Fmoc group with a solution comprising an amine base to provide an N-terminus;
q) repeating steps n) through p) sequentially, replacing the Fmoc-Thr(tBu)$^{33}$-OH with the following series of Fmoc-protected amino acids: His(Trt)$^{32}$-OH, Leu$^{30}$-OH, (Boc)Lys$^{30}$-OH, Aib$^{29}$-OH, Leu$^{28}$-OH, Leu$^{27}$-OH, (Boc)Lys$^{26}$-OH, (OtBu)Glu$^{23}$-OH, Leu$^{24}$-OH, Leu$^{23}$-OH, (OtBu)Glu$^{22}$-OH, (Pbf)Arg$^{21}$-OH, (Pbf)-Arg$^{20}$-OH, (Pbf)Arg$^9$-OH, Leu$^{18}$-OH, and (OtBu)Asp$^{17}$-OH.

In some embodiments, capping the resin comprises allowing any unreacted linker present on the resin to react with an acetylation reagent to avoid any the undesired peptide chain formation. In some embodiments, the acetylation reagent is acetic anhydride and pyridine in dichloromethane.

The coupling and selective Fmoc removal are each conducted as disclosed herein above.

Generally, a Kaiser test is performed after each coupling to ensure complete incorporation of the desired amino acid residue. If the Kaiser test is slightly positive (pale blue), the coupling reaction is repeated using 0.15 molar equivalents of the appropriate Fmoc-amino acid. If the Kaiser test is positive (dark blue), the coupling reaction is repeated using a full 1.5 molar equivalents of the appropriate Fmoc-amino acid. In some embodiments, the method comprises utilizing a tiered approach to the Kaiser test as described herein above. In some embodiments, the tiered approach is utilized for introduction of amino acid 18 ($Leu^{18}$).

Certain amino acid couplings have been routinely observed as failing to go to completion. Particularly, introduction of Fmoc-Aib-OH and Fmoc-Leu-OH, residues 29 and 28, respectively, often fail to go to completion. Accordingly, in some embodiments, each of the respective coupling reactions is repeated prior to continuing the sequential coupling reactions to ensure full incorporation of the $Aib^{29}$ and $Leu^{28}$ residues.

In another aspect is provided a process for the preparation of abaloparatide comprising:
a) anchoring Fmoc-protected alanine (Fmoc-$Ala^{34}$-OH) to Rink amide 4-methylbenzhydrylamine (MBHA) resin;
b) capping the resin obtained in step a) by acetylation;
c) selectively cleaving the Fmoc group with a solution comprising piperidine to provide an N-terminus;
d) coupling a carboxyl terminus of Fmoc-Thr(tBu)$^{33}$-OH to the N-terminus in the presence of a coupling reagent comprising benzotriazol-1-yloxytripyrrolidinophosphonium hexafluorophosphate (PyBOP), 1-Hydroxybenzotriazole (HOBt), N,N'-diisopropylcarbodiimide (DIC), and diisopropylethylamine (DIEA), performing a Kaiser and/or Chloranil test after each step d) to confirm complete incorporation of each Fmoc-protected amino acid, and repeating said step d) if a positive Kaiser or Chloranil test result is obtained;
e) selectively cleaving the Fmoc group with a solution comprising piperidine to provide an N-terminus;
f) repeating steps d) and e) sequentially, replacing the Fmoc-Thr(tBu)$^{33}$-OH with the following series of Fmoc-protected amino acids: His(Trt)$^{32}$-OH, Leu$^{31}$-OH, (Boc)Lys$^{30}$-OH, Aib$^{29}$-OH, Leu$^{28}$-OH, Leu$^{27}$-OH, (Boc)Lys$^{26}$-OH, (OtBu)Glu$^{23}$-OH, Leu$^{24}$-OH, Leu$^{23}$-OH, (OtBu)Glu$^{22}$-OH, (Pbf)Arg$^{21}$-OH, (Pbf)-Arg$^{20}$-OH, (Pbf)Arg$^{19}$-OH, Leu$^{18}$-OH, and (OtBu)Asp$^{17}$-OH, and performing a Kaiser and/or Chloranil test after each step d) before each step e) to confirm complete incorporation of each Fmoc-protected amino acid, and repeating said step d) if a positive Kaiser or Chloranil test result is obtained;
g) coupling a carboxyl terminus of Fmoc-(Trt)Gln$^{16}$-OH to the N-terminus in the presence of a coupling reagent comprising PyBOP, HOBt, DIC, and DIEA;
h) repeating step g) to ensure complete incorporation of Fmoc-(Trt)Gln$^{16}$;
i) selectively cleaving the Fmoc group with a solution comprising piperidine to provide an N-terminus;
j) coupling a carboxyl terminus of Fmoc-Ile$^{15}$-OH to the N-terminus in the presence of a coupling reagent comprising PyBOP, HOBt, DIC, and DIEA;
k) selectively cleaving the Fmoc group with a solution comprising piperidine to provide an N-terminus;
l) repeating steps j) and k) sequentially, replacing Fmoc-Ile$^{15}$-OH with the following series of Fmoc-protected amino acids: Ser (tBu)$^{14}$-OH, Lys (Boc)$^{13}$-OH, Gly$^{12}$-OH, Lys(Boc)$^{11}$-OH, Asp(OtBu)$^{10}$-OH, His(Trt)$^{9}$-OH, Leu$^{8}$-OH, Leu7-OH, Gln(Trt)$^{6}$-OH, His (Trt)$^{5}$-OH, Glu (OtBu)$^{4}$-OH, Ser(tBu)$^{3}$-OH, Val$^{2}$-OH, and Ala$^{1}$-OH;
m) performing a Kaiser and/or Chloranil test after each step j) before each step k) to confirm complete incorporation of each Fmoc-protected amino acid, and repeating said step j) if a positive Kaiser or Chloranil test result is obtained; and
n) treating the resulting anchored, protected abaloparatide with a solution comprising trifluoroacetic acid to provide crude abaloparatide.

Each of the steps b-n is performed as disclosed herein above. In some embodiments, the process is performed in accordance with the description in the following Table 2:

TABLE 2

Exemplary process for abaloparatide preparation.

| Step # | Amino Acid # | Reaction | Conditions | Monitoring Test |
|---|---|---|---|---|
| 1 | 34 | Load Fmoc-Ala-OH on to Rink amid MBHA resin | Amino acid: 1.05 eq.; DIC: 2x1.05 eq; HOBT: 1.05 eq.: PyBOP: 1.05 eq.; DIPEA, pH 7 | HPLC |
| 2 | | Acetylation of unreacted amine | Ac$_2$O (5 eq) and pyridine (5 eq) DMF | Kaiser test |
| 3 | | Fmoc deprotection | 20% piperidine in DMF | |
| 4 | 33 | Couple Fmoc-Thr(tBu)-OH | Amino acid: 1.5 eq. DIC 2x1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 5 | | Fmoc deprotection | 20% piperidine in DMF | |
| 6 | 32 | Couple Fmoc-His(Trt)-OH | Amino acid: 1.5 eq.; DIC 2x1.5 eq.; HOBT: 1.5 eq: PyBOP: 0.25 eq.; DIPEA, pH 7 | Kaiser test; if Kaiser test slightly positive, repeat coupling with 0.15 eq AA; if positive, repeat with 1.5 eq |

TABLE 2-continued

Exemplary process for abaloparatide preparation.

| Step # | Amino Acid # | Reaction | Conditions | Monitoring Test |
|---|---|---|---|---|
| 7 | | Fmoc deprotection | 20% piperidine in DMF | |
| 8 | 41 | Couple Fmoc-Leu-OH | Amino acid: 1.5 eq.; DIC 2×1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 9 | | Fmoc deprotection | 20% piperidine in DMF | |
| 10 | 30 | Couple Fmoc-Lys(Boc)-OH | Amino acid: 1.5 eq.; DIC 2×1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 11 | | Fmoc deprotection | 20% piperidine in DMF | |
| 12 | 29 | Couple Fmoc-Aib-OH | Amino acid: 1.5 eq.; DIC 2×1.5 eq.; HOBT: 1.5 eq.; PyBOP: 0.25 eq.; DIPEA, pH 7 | N/A |
| 13 | 29 | Couple Fmoc-Aib-OH | Amino acid: 1.5 eq.; DIC 2×1.5 eq.; HOBT: 1.5 eq.; PyBOP: 0.25 eq.; DIPEA, pH 7 | |
| 14 | | Fmoc deprotection | 20% piperidine in DMF | |
| 15 | 28 | Couple Fmoc-Leu-OH | Amino acid: 1.5 eq.; DIC 2×1.5 eq.; HOBT: 1.5 eq.; PyBOP: 0.25 eq.; DIPEA, pH 7 | N/A |
| 16 | 28 | Couple Fmoc-Leu-OH | Amino acid: 1.5 eq.; DIC 2×1.5 eq.; HOBT: 1.5 eq.; PyBOP: 0.25 eq.; DIPEA, pH 7 | |
| 17 | | Fmoc deprotection | 20% piperidine in DMF | |
| 18 | 27 | Couple Fmoc-Leu-OH | Amino acid: 1.5 eq.; DIC 2×1.5 eq.; HOBT: 1.5 eq.; PyBOP: 0.25 eq.: DIPEA, pH 7 | Kaiser test; if Kaiser test slightly positive, repeat coupling with 0.15 eq AA; if positive, repeat with 1.5 eq |
| 19 | | Fmoc deprotection | 20% piperidine in DMF | |
| 20 | 26 | Couple Fmoc-Lys(Boc)-OH | Amino acid: 1.5 eq.; DIC 2×1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 21 | | Fmoc deprotection | 20% piperidine in DMF | |
| 22 | 25 | Couple Fmoc-Glu(OtBu)-OH | Amino acid: 1.5 eq.; DIC 2×1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 23 | | Fmoc deprotection | 20% piperidine in DMF | |
| 24 | 24 | Couple Fmoc-Leu-OH | Amino acid: 1.5 eq.; DIC 2×1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 25 | | Fmoc deprotection | 20% piperidine and 2% HOBt in DMF | |
| 26 | 23 | Couple Fmoc-Leu-OH | Amino acid: 1.5 eq.; DIC 2×1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 27 | | Fmoc deprotection | 20% piperidine and 2% HOBt in DMF | |
| 28 | 22 | Couple Fmoc-Glu(OtBu)-OH | Amino acid: 1.5 eq.; DIC 2×1.5 eq.; HOBT: 1.5 eq.; PyBOP: 0.25 eq.; DIPEA, pH 7 | Kaiser test: if Kaiser test slightly positive, repeat coupling with 0.15 eq AA; if positive, repeat with 1.5 eq |
| 29 | | Fmoc deprotection | 20% piperidine and 2% HOBt in DMF | |

TABLE 2-continued

Exemplary process for abaloparatide preparation.

| Step # | Amino Acid # | Reaction | Conditions | Monitoring Test |
|---|---|---|---|---|
| 30 | 21 | Couple Fmoc-Arg(Pbf)-OH | Amino acid: 1.5 eq.; DIC 2x1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 31 | | Fmoc deprotection | 20% piperidine and 2% HOBt in DMF | |
| 32 | 20 | Couple Fmoc-Arg(Pbf)-OH | Amino acid: 1.5 eq.; DIC 2x1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 33 | | Fmoc deprotection | 20% piperidine and 2% HOBt in DMF | |
| 34 | 19 | Couple Fmoc-Arg(Pbf)-OH | Amino acid: 1.5 eq.; DIC 2x1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 35 | | Fmoc deprotection | 20% piperidine and 2 % HOBt in DMF | |
| 36 | 18 | Couple Fmoc-Leu-OH | Amino acid: 1.5 eq.; DIC 2×1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 37 | | Fmoc deprotection | 20% piperidine and 2% HOBt in DMF | |
| 38 | 17 | Couple Fmoc-Asp(OtBu)-OH | Amino acid: 1.5 eq.; DIC 2x1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 39 | | Fmoc deprotection | 20% piperidine and 2% HOBt in DMF | |
| 40 | 16 | Couple Fmoc-Gln(Trt)-OH | Amino acid: 1.5 eq.; DIC 2x1.5 eq.; HOBT: 1.5 eq.; PyBOP: 0.25 eq.; DIPEA, pH 7 | N/A |
| 41 | 16 | Couple Fmoc-Gln(Trt)-OH | Amino acid: 1.5 eq.; DIC 2x1.5 eq.; HOBT: 1.5 eq.: PyBOP: 0.25 eq.; DIPEA, pH 7 | |
| 42 | | Fmoc deprotection | 20% piperidine in DMF | |
| 43 | 15 | Couple Fmoc-De-OH | Amino acid: 1.5 eq; DIC 2x1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 44 | | Fmoc deprotection | 20% piperidine and 2% HOBt in DMF | |
| 45 | 14 | Couple Fmoc-Ser(tBu)-OH | Amino acid: 1.5 eq.; DIC 2x1.5 eq.; HOBT: 1.5 eq.; PyBOP: 0.25 eq.; DIPEA, pH 7 | Kaiser test: if Kaiser test slightly positive, repeat coupling with 0.15 eq AA; if positive, repeat with 1.5 eq |
| 46 | | Fmoc deprotection | 20% piperidine and 2% HOBt in DMF | |
| 47 | 13 | Couple Fmoc-Lys(Boc)-OH | Amino acid: 1.5 eq.; DIC 2x1.5 eq.; HOBT: 1.5 eq.; PyBOP: 0.25 eq.; DIPEA, pH 7 | Kaiser test; if Kaiser test slightly positive, repeat coupling with 0.15 eq AA; if positive, repeat with 1.5 eq |
| 48 | | Fmoc deprotection | 20% piperidine and 2% HOBt in DMF | |
| 49 | 12 | Couple Fmoc-Gly-OH | Amino acid: 1.5 eq.; DIC 2x1.5 eq.; HOBT: 1.5 eq.; PyBOP: 0.25 eq.; DIPEA, pH 7 | Kaiser test: if Kaiser test slightly positive, repeat coupling with 0.15 eq AA; if positive, repeat with 1.5 eq |
| 50 | | Fmoc deprotection | | |
| 51 | 11 | Couple Fmoc-Lys(Boc)-OH | Amino acid: 1.5 eq.; DIC 2x1.5 eq.; | Kaiser test; if Kaiser test slightly positive, repeat |

TABLE 2-continued

Exemplary process for abaloparatide preparation.

| Step # | Amino Acid # | Reaction | Conditions | Monitoring Test |
|---|---|---|---|---|
| | | | HOBT: 1.5 eq ::<br>PyBOP: 0.25 eq.;<br>DIPEA, pH 7 | coupling with 0.15 eq AA;<br>if positive, repeat with<br>1.5 eq |
| 52 | | Fmoc deprotection | 20% piperidine and<br>2% HOBt in DMF | |
| 53 | 10 | Couple Fmoc-Asp(OtBu)-OH | Amino acid: 1.5 eq.;<br>DIC 2x1.5 eq.;<br>HOBT: 1.5 eq.;<br>PyBOP: 0.25 eq.;<br>DIPEA, pH 7 | Kaiser test; if Kaiser test<br>slightly positive, repeat<br>coupling with 0.15 eq AA;<br>if positive, repeat with<br>1.5 eq |
| 54 | | Fmoc deprotection | 20% piperidine and<br>2% HOBt in DMF | |
| 55 | 9 | Couple Fmoc-His(Trt)-OH | Amino acid: 1.5 eq.;<br>DIC 2x1.5 eq.;<br>HOBT: 1,5 eq.;<br>PyBOP: 0.25 eq.;<br>DIPEA, pH 7 | Kaiser test; if Kaiser test<br>slightly positive, repeat<br>coupling with 0.15 eq AA;<br>if positive, repeat with<br>1.5 eq |
| 56 | | Fmoc deprotection | | |
| 57 | 8 | Couple Fmoc-Leu-OH | Amino acid: 1.5 eq.;<br>DIC 2x1.5 eq.;<br>HOBT: 1.5 eq.;<br>PyBOP: 0.25 eq.;<br>DIPEA, pH 7 | Kaiser test; if Kaiser test<br>slightly positive, repeat<br>coupling with 0.15 eq AA;<br>if positive, repeat with<br>1.5 eq |
| 58 | | Fmoc deprotection | 20% piperidine and<br>2% HOBt in DMF | |
| 59 | 7 | Couple Fmoc-Leu-OH | Amino acid: 1.5 eq.<br>DIC 2x1.5 eq.;<br>HOBT: 1.5 eq.;<br>PyBOP: 0.25 eq.;<br>DIPEA, pH 7 | Kaiser test: if Kaiser test<br>slightly positive, repeat<br>coupling with 0.15 eq AA;<br>if positive, repeat with<br>1.5 eq |
| 60 | | Fmoc deprotection | 20% piperidine and<br>2% HOBt in DMF | |
| 61 | 6 | Couple Fmoc-Gln(Trt)-OH | Amino acid: 1.5 eq.;<br>DIC 2×1.5 eq.;<br>HOBT: 1.5 eq ;;<br>PyBOP: 0.25 eq.;<br>DIPEA, pH 7 | Kaiser test; if Kaiser test<br>slightly positive, repeat<br>coupling with 0.15 eq AA;<br>if positive, repeat with<br>1.5 eq |
| 62 | | Fmoc deprotection | 20% piperidine and<br>2% HOBt in DMF | |
| 63 | 5 | Couple Fmoc-His(Trt)-OH | Amino acid: 1.5 eq.;<br>DIC 2x1.5 eq.;<br>HOBT: 1.5 eq.;<br>PyBOP: 0.25 eq.;<br>DIPEA, pH 7 | Kaiser test; if Kaiser test<br>slightly positive, repeat<br>coupling with 0.15 eq AA;<br>if positive, repeat with<br>1.5 eq |
| 64 | | Fmoc deprotection | 20% prperidine and<br>2% HOBt in DMF | |
| 65 | 4 | Couple Fmoc-Glu(OtBu)-OH | Amino acid: 1.5 eq.;<br>DIC 2x1.5 eq.;<br>HOBT: 1.5 eq.;<br>PyBOP: 0.25 eq.;<br>DIPEA, pH 7 | Kaiser test; if Kaiser test<br>slightly positive, repeat<br>coupling with 0.15 eq AA;<br>if positive, repeat with<br>1.5 eq |
| 66 | | Fmoc deprotection | 20% piperidine and 2% HOBt DMF | |
| 67 | 3 | Couple Fmoc-Ser(tBu)-OH | Amino acid: 1.5 eq.;<br>DIC 2x1.5 eq.;<br>HOBT: 1.5 eq.;<br>PyBOP: 0.25 eq.;<br>DIPEA, pH 7 | Kaiser test: if Kaiser test<br>slightly positive, repeat<br>coupling with 0.15 eq AA;<br>if positive, repeat with<br>1.5 eq |
| 68 | | Fmoc deprotection | 20% piperidine and 2% HOBt DMF | |
| 69 | 2 | Couple Fmoc-Val-OH | Amino acid: 1.5 eq.;<br>DIC 2x1.5 eq.;<br>HOBT: 1.5 eq.;<br>PyBOP: 0.25 eq.;<br>DIPEA, pH 7 | Kaiser test: if Kaiser test<br>slightly positive, repeat<br>coupling with 0.15 eq AA,<br>if positive, repeat with<br>1.5 eq |
| 70 | | Fmoc deprotection | 20% piperidine and<br>2% HOBt in DMF | |
| 71 | 1 | Couple Fmoc-Ala-OH | Amino acid: 1.5 eq.;<br>DIC 2x1.5 eq.;<br>HOBT: 1.5 eq.;<br>PyBOP: 0.25 eq.;<br>DIPEA, pH 7 | Kaiser test; if Kaiser test<br>slightly positive, repeat<br>coupling with 0.15 eq AA;<br>if positive, repeat with<br>1.5 eq |
| 72 | | Cleave from resin and deprotect all acid labile groups | TFA/H$_2$O/TIS/EDT:<br>92.5/2.5/2.5/2.5 (v/v/v/v), | HPLC/UPLC |

In some embodiments, the process comprises utilizing a tiered approach to the Kaiser test as described herein above. In some embodiments, the tiered approach is utilized for introduction of amino acid 18 (Leu$^{18}$).

The crude abaloparatide, obtained according to the disclosed methods, generally contains less than about 1% of des-Gln$^{16}$-abaloparatide by weight, based on the total weight of the crude abaloparatide. In some embodiments, the obtained crude abaloparatide contains less than about 0.5%, or less than about 0.3%, or even about 0.1%, of des-Gln$^{16}$ abaloparatide by weight, based on the total weight of the crude abaloparatide.

In some embodiments, the process further comprises purification of the abaloparatide. Such purification may comprise washing, precipitation, chromatography (e.g., HPLC and/or UPLC), and combinations thereof.

Embodiments of the present disclosure can be further defined by reference to the following non-limiting examples. It will be apparent to those skilled in the art that many modifications, both to materials and methods, can be practiced without departing from the scope of the present disclosure.

EXEMPLIFICATION

General Methods
Kaiser Test

A Kaiser Test is used for monitoring completion of each coupling step during the synthesis of abaloparatide. The Test is performed according top the following protocol. At the end of each coupling sequence, samples (manually approximating 40-50 peptide resin beads) is withdrawn from the reactor to glass tubes. Four tubes are prepared in total: two tubes each containing about 40-50 peptide-resin beads; a positive blank containing the corresponding free amino acid reference standard; and a negative blank, which is an empty tube. To each tube is added sequentially:

3 drops phenol reagent
3 drops KCN reagent
3 drops ninhydrin

The samples are homogenized and the tubes held at a temperature of 100° C. for 3 minutes and 30 seconds. The positive blank is analyzed to be certain a blue color is obtained. If not, reagents should be replaced and the test repeated. A Negative test (K−) is signified by the presence of a yellow color for the supernatant liquid and colorless resin in both test samples. A Lightly Positive test (Kl+) is signified by the presence of a light blue resin or supernatant color in both test samples. A Positive test (K+) is signified by the presence of a blue resin and/or supernatant color in both test samples.

Example 1. Preparation of H-[16-34]-NH$_2$ (Reference)

A batch of the 19-amino acid peptide, NH$_2$-Gln$^{16}$(Trt)-Asp$^{17}$(OtBu)-Leu-Arg(Pbf)-Arg$^{20}$-(Pbf)-Arg(Pbf)-Glu(OtBu)-Leu-Leu-Glu$^{25}$-(OtBu)-Lys(Boc)-Leu-Leu-Aib-Lys$^{30}$-(Boc)-Leu-His(Trt)-Thr(tBu)-Ala$^{34}$ (H-[16-34]-NH$_2$), bound to Rink amide MBHA resin (SEQ ID NO:2), was prepared by successively coupling and Fmoc-deprotecting a series of Fmoc-protected amino acids to alanine bound to Rink amide resin. The couplings were performed with 1.5 equivalents of the amino acid, 2×1.5 eq. of DIC, 1.5 eq. of HOBT, 0.25 eq. of PyBOP, and DIPEA at pH 7. A Kaiser test was performed after each coupling reaction, and coupling repeated in the absence of a negative result. Deprotection of the Fmoc group following each coupling was performed using 20% piperidine in DMF.

A 1 g sample of the batch was triturated with DCM, followed by trituration with isopropanol. This operation was repeated four times. The peptide-resin was dried for 1 hr in a vacuum oven at a temperature of 25±5° C. A fresh cleavage cocktail containing TFA (14.2 ml, 185.4 mmol, 412.00 equiv.), EDT (0.22 ml, 2.27 mmol, 6.00 equiv.), TIS (0.32 ml, 1.6 mmol, 3.55 equiv.) and H$_2$O (0.25 ml, 13.8 mmol, 30.66 equiv.) was prepared, and the dried peptide-resin was slowly added to the cleavage cocktail at room temperature. The resulting suspension was stirred at 35° C. for 30 min. The reaction was quenched using 100 ml of DIPE. The resulting suspension was centrifuged and the supernatant removed. The remaining pellet was suspended in 100 ml of DIPE. The resulting suspension was centrifuged and the supernatant removed. The pellet was dissolved in HPLC injection solvent for analysis. This sample is referred to herein as H-[16-34]-NH$_2$ (1).

A second, third, and fourth sample was obtained from further batches of material identically prepared, and are referred to herein as H-[16-34]-NH$_2$ (2), H-[16-34]-NH$_2$ (3), and H-[16-34]-NH$_2$ (4), respectively.

Figure 3:
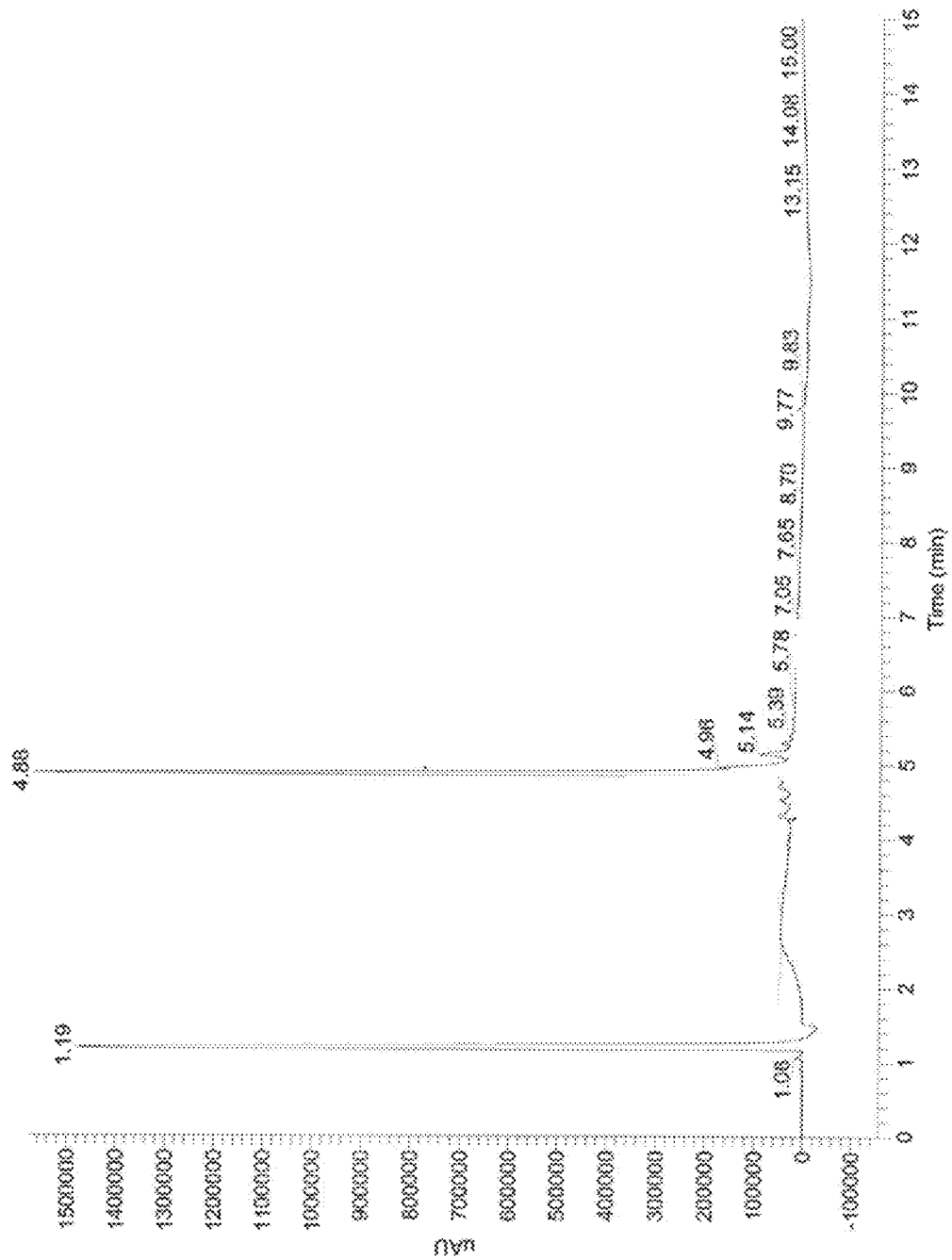
FIG. 3 is an exemplary HPLC-Mass Spectroscopy (LC-MS) trace of a reference peptide sample.
Figure 4:
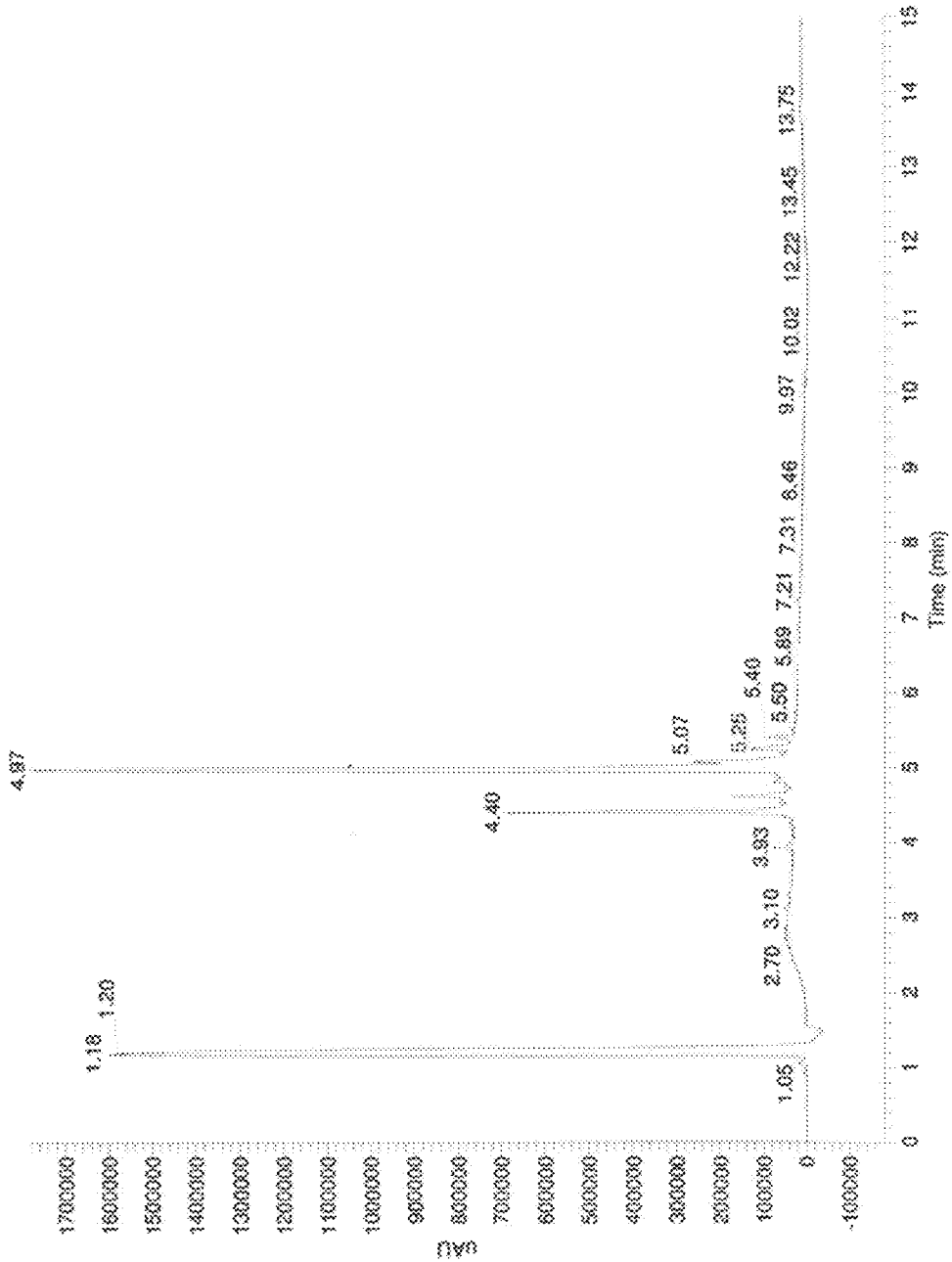
FIG. 4 is an exemplary LC-MS trace of a reference peptide sample.

Each sample was analyzed by HPLC. The results are provided in Table 3, FIG. 3 and FIG. 4. A Gln$^{16}$ deletion was observed at a level of 5.45% (MS rel.) for H-[16-34]-NH$_2$ (1) (FIG. 3), while it was observed at a level of 49.44% (MS rel.) for H-[16-34]-NH$_2$ (2) (FIG. 4). The deletion impurity was observed at 22.9% and 0.25% in batches 3 and 4, respectively.

TABLE 3

Relative retention time (RRT) and % of Gln$^{16}$ deletion product for H-[17-34]-NH$_2$ peptides prepared according to reference method

| Sample | RRT | MS rel % | Identification |
|---|---|---|---|
| H-[16-34]-NH$_2$ (1) | 0.885 | 5.45 | H-[17-34]-NH$_2$ |
| H-[16-34]-NH$_2$ (2) | 0.883 | 49.44 | Mw = 2187.33 g/mol |
| H-[16-34]-NH$_2$ (3) | 1.062 | 22.9 | |
| H-[16-34]-NH$_2$ (4) | 1.067 | 0.25 | |

Example 2. Preparation of H-[16-34]-NH$_2$ Using Recoupling Procedure

In order to determine if a recoupling of Gln$^{16}$ would avoid a deletion, the following experiment was performed.

To a suspension of the peptide-resin of Example 1 (H-[17-34]-NH$_2$, bound to Rink amide MBHA resin; 1 g, target substitution: 0.45 mmol, 1.0 equiv.) in DMF (6.5 ml) was added dropwise at room temperature a freshly prepared solution of Fmoc-Gln(trt)-OH (1.05 equiv.) and PyBOP (0.25 equiv.) in DMF (3.0 ml). The reaction mixture was stirred at room temperature and its pH was adjusted to pH 7 using a solution of DIPEA/DMF (20:80). After 30 minutes of reaction with a pH stable at a value of 7, the suspension was filtered and the solids triturated and washed 5 times with DMF (2.0 ml).

The solid sample was triturated with DCM, followed by trituration with isopropanol. This operation was repeated four times. The peptide-resin was dried for 1 hr in a vacuum oven at a temperature of 25±5° C. A fresh cleavage cocktail containing TFA (14.2 ml, 185.4 mmol, 412.00 equiv.), EDT (0.22 ml, 2.27 mmol, 6.00 equiv.), TIS (0.32 ml, 1.6 mmol, 3.55 equiv.) and H$_2$O (0.25 ml, 13.8 mmol, 30.66 equiv.) was prepared, and the dried peptide-resin was slowly added to the cleavage cocktail at room temperature. The resulting suspension was stirred at 35° C. for 30 min. The reaction was quenched using 100 ml of DIPE. The resulting suspension was centrifuged and the supernatant removed. The remaining pellet was suspended in 100 ml of DIPE. The resulting suspension was centrifuged and the supernatant removed. The pellet was dissolved in HPLC injection solvent for analysis. This sample is referred to herein as H-[16-34]-$NH_2$ (5).

A second, third, and fourth sample was obtained from further batches of material identically prepared, and are referred to herein as H-[16-34]-$NH_2$ (6-8).

Figure 5:
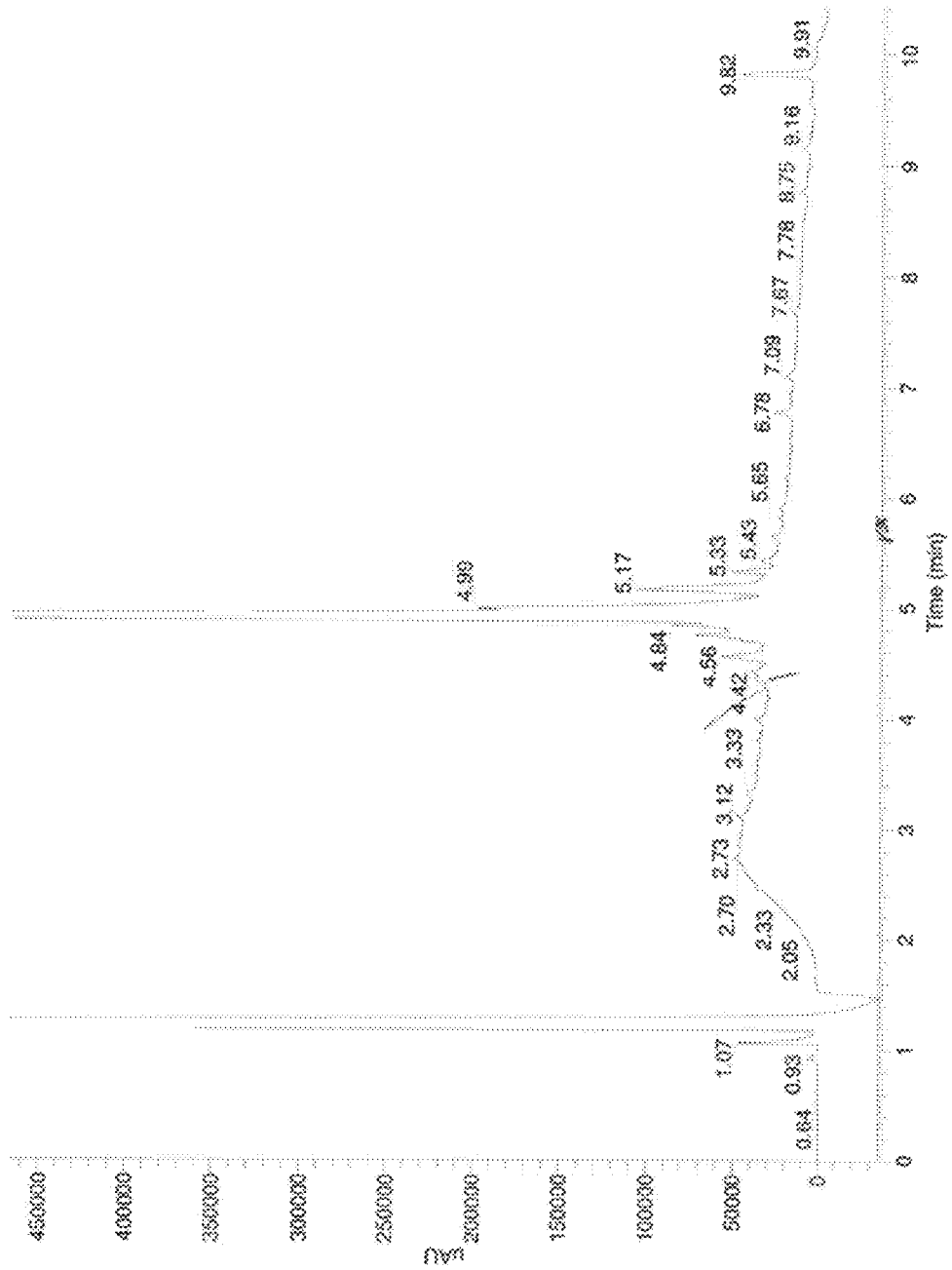
FIG. 5 is an exemplary LC-MS trace of a peptide sample according to a non-limiting embodiment of the disclosed method.
Figure 6:
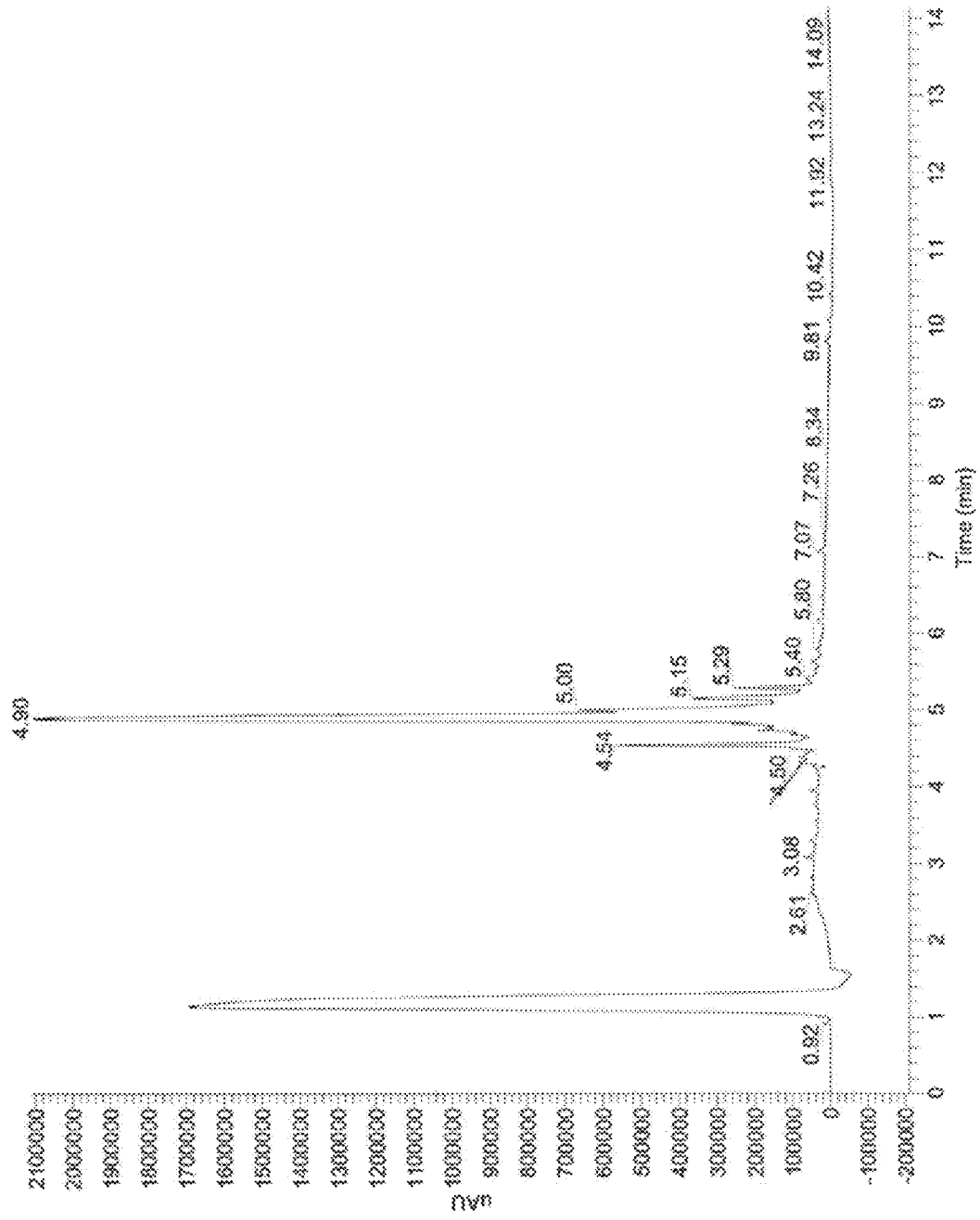
FIG. 6 is an exemplary LC-MS trace of a peptide sample prepared according to a non-limiting embodiment of the disclosed method.

Each sample was analyzed by HPLC. The results are provided in Table 4, FIG. 5 and FIG. 6. A $Gln^{16}$ deletion was observed at a level of 0.35% (MS rel.) for H-[16-34]-$NH_2$ (3) (FIG. 5), while it was observed at a level of 0.96% (MS rel.) for H-[16-34]-$NH_2$ (4) (FIG. 6).

TABLE 4

Relative retention time (RRT) and % of $Gln^{16}$ deletion product for H-[17-34]-$NH_2$ peptides prepared according to inventive method.

| Sample | RRT | MS rel % | Identification |
|---|---|---|---|
| H-[16-34]-$NH_2$ (5) | 0.892 | 0.35 | H-[17-34]-NH2 |
| H-[16-34]-$NH_2$ (6) | 0.885 | 0.96 | Mw = 2187.33 g/mol |
| H-[16-34]-$NH_2$ (7) | 1.067 | 0.40 | |
| H-[16-34]-$NH_2$ (8) | 1.070 | 0.23 | |

The results indicate that performing a recoupling reaction of $Gln^{16}$ without regard to Kaiser test outcome leads to a tremendous reduction in undesired $Gln^{16}$ deletion product, relative to the deletion product present when no recoupling is performed, and/or when performing such recoupling relies on the often false-negative Kaiser test result.

Example 3. Preparation of H-[16-34]-$NH_2$ Using Recoupling Procedure

Batches of the 34-amino acid peptide abaloparatide ($Ala^1$-Val-Ser-Glu-$His^5$-Gln-Leu-Leu-His-$Asp^{10}$-Lys-Gly-Lys-Ser-$Ile^{15}$-Gln-Asp-Leu-Arg-$Arg^{20}$-Arg-Glu-Leu-Leu-$Glu^{25}$-Lys-Leu-Leu-Aib-$Lys^{30}$-Leu-His-Thr-$Ala^{34}$-$NH_2$; SEQ ID NO: 1) were prepared on 250 mmol and 826 mmol scales (230 to 320 grains and 1000 to 1400 grams, respectively) using the preparative methods described herein and in Example 2. In each instance, the Kaiser Test was performed to confirm complete coupling for all amino acids, except amino acids 29, 28, and 16, where a systematic recoupling was performed. For amino acid 18, a tiered approach for the Kaiser Test was performed if a slightly positive Kaiser Test result was obtained.

Following the final coupling and washing step, the side chain protecting groups and the peptide-resin bond were cleaved by stirring the protected peptide-resin for about 3 hours at about 20° C. in solution of TFA, TIS, water, and ethanedithiol (92.5/2.5/2.5/2.5, V/V/V/V). The volume of the solution was approximately 10 liters per kilogram of the peptide-resin. The peptide was extracted by filtration, and the resin further washed 3 times with TFA (about 2 L per kg of peptide/resin for each washing cycle). The combined filtrates were concentrated under reduced pressure at a temperature of 25° C. or less. The peptide was precipitated from the concentrated solution by addition of diisopropyl ether (DIPE). The peptide was filtered, washed with DIPE, then with DIPE/$CH_3CN$ (1/1), then with DIPE alone, and dried under reduced pressure.

The crude peptide was dissolved in AcOH/$H_2O$/$CH_3CN$ 10/88/2% V/V/V and filtered on a 5 μm cut-off cartridge, then on a 0.6 μm cut-off cartridge prior to purification by preparative HPLC using the following conditions:
  Stationary phase: C18 Silica 10 μm—100 Å (Kromasil or equivalent)
  Mobile phase A: TFA/H2O/CH3CN: 0.1/97.9/2.0 (V/V/V)
  Mobile phase B: TFA/H2O/CH3CN: 0.1/49.9/50.0 (V/V/V)
  Loading: ≤34 g crude powder/kg stationary phase
  Purification gradient:
    0% B during 15 min,
    0% B to 35% B over 5 min
    35% to 65% B over 60 min
  Flow rate: 3.3±0.1 cm/min
  UV detection: 220 nm Collected fractions were pooled and concentrated to give the purified product. Further secondary and/or tertiary purifications were performed as necessary. The isolated product from each batch met the appropriate acceptance criteria.

We claim:

1. A process for the preparation of abaloparatide comprising:
   a) providing a peptide bound to a solid resin and having an initial N-terminus, wherein said bound peptide is NH$_2$-Asp(OtBu)-Leu-Arg(Pbf)-Arg$^{20}$(Pbf)-Arg(Pbf)-Glu(OtBu)-Leu-Leu-Glu$^{25}$(OtBu)-Lys(Boc)-Leu-Leu-Aib-Lys$^{30}$(Boc)-Leu-His(Trt)-Thr(tBu)-Ala$^{34}$-Rink Amide MBHA resin (SEQ ID NO: 2);
   b) coupling a carboxyl terminus of Fmoc-(Trt)Gln$^{16}$-OH to the initial N-terminus of the bound peptide, wherein coupling comprises adding to a suspension of the bound peptide in dimethylformamide from about 1.05 to about 2 molar equivalents of Fmoc-(Trt)Gln$^{16}$-OH, relative to the bound peptide, in the presence of benzotriazol-1-yloxytripyrrolidinophosphonium hexafluorophosphate (PyBOP), 1-Hydroxybenzotriazole (HOBt), N,N'-diisopropylcarbodiimide (DIC), and diisopropylethylamine (DIEA), and allowing the mixture to react for a period of time;
   c) adding to the mixture a further from about 1.05 to about 2 molar equivalents of Fmoc-(Trt)Gln$^{16}$-OH, relative to the bound peptide, in the presence of additional PyBOP, HOBt, DIC, and DIEA;
   d) selectively cleaving the Fmoc group with a solution comprising an amine base to provide a peptide bound to a solid resin and having a new N-terminus.

2. The process of claim 1, wherein the amine base is piperidine.

3. The process of claim 2, wherein the piperidine is present as an approximately 20% solution by weight in DMF.

4. The process of claim 1, further comprising
   e) coupling a carboxyl terminus of Fmoc-Ile$^{15}$-OH to the new N-terminus in the presence of a coupling reagent;
   f) selectively cleaving the Fmoc group with a solution comprising an amine base to provide a peptide bound to the solid resin and having a new N-terminus; and
   g) repeating steps e) and f), wherein each step e) is performed, in sequential order, substituting the Fmoc-Ile$^{15}$-OH with the following Fmoc-protected amino acids: Ser(tBu)$^{14}$-OH, Lys(Boc)$^{13}$-OH, Gly$^{12}$-OH, Lys(Boc)$^{11}$-OH, Asp$^{10}$(OtBu)-OH, His(Trt)$^9$-OH, Leu$^8$-OH, Leu$^7$-OH, Gln(Trt)$^6$-OH, His$^5$(Trt)-OH, Glu(OtBu)$^4$-OH, Ser(tBu)$^3$-OH, Val$^2$-OH, and Ala$^1$-OH, to form a thirty-four amino acid peptide sequence bound to the solid resin.

5. The process of claim 4, wherein the coupling reagent comprises PyBOP, HOBt, DIC, and DIEA.

6. The process of claim 4, wherein each coupling step e) is performed using from about 1.05 to about 2 molar equivalents of the Fmoc-amino acid, relative to the bound peptide.

7. The process of claim 4, wherein the amine base is piperidine.

8. The process of claim 7, wherein the piperidine is present as an approximately 20% solution by weight in DMF.

9. The process of claim 4, further comprising:
   performing a Kaiser and/or Chloranil test after each step e) but before each step f) to confirm complete incorporation of each Fmoc-protected amino acid; and
   performing a recoupling reaction if a positive Kaiser or Chloranil test result is obtained.

10. The process of claim 9, wherein performing the recoupling reaction comprises performing a coupling reaction with the Fmoc-protected amino acid one or more additional times, using from 0.15 to 1.5 molar equivalents of the respective Fmoc-amino acid relative to the bound peptide, repeating said coupling until a negative Kaiser or Chloranil test result is obtained.

11. The process of claim 4, further comprising:
    treating the thirty-four amino acid peptide sequence bound to the solid resin with a solution comprising trifluoroacetic acid to provide crude abaloparatide.

12. The process of claim 11, wherein the crude abaloparatide contains less than about 1% of des-Gln$^{16}$-abaloparatide by weight, based on the total weight of the crude abaloparatide.

13. The process of claim 11, wherein the crude abaloparatide contains less than about 0.5% des-Gln$^{16}$-abaloparatide by weight, based on the total weight of the crude abaloparatide.

14. The process of claim 11, wherein the crude abaloparatide contains less than about 0.3% des-Gln$^{16}$-abaloparatide by weight, based on the total weight of the crude abaloparatide.

15. The process of claim 4, wherein providing the peptide bound to the solid resin comprises:

anchoring Fmoc-protected alanine (Fmoc-Ala$^{34}$-OH) to Rink amide 4-methylbenzhydrylamine (MBHA) resin;

capping the resin obtained in the anchoring step by acetylation;

selectively cleaving the Fmoc group with a solution comprising an amine base to provide an N-terminus;

coupling a carboxyl terminus of Fmoc-Thr(tBu)$^{33}$-OH to the N-terminus in the presence of a coupling reagent;

performing a Kaiser and/or Chloranil test after each coupling step to confirm complete incorporation of each Fmoc-protected amino acid, and performing a recoupling reaction if a positive Kaiser or Chloranil test result is obtained;

selectively cleaving the Fmoc group with a solution comprising an amine base to provide an N-terminus; and repeating sequentially each of the coupling, performing a Kaiser and/or Chloranil test, and selectively cleaving the Fmoc group steps, in each instance replacing the Fmoc-Thr(tBu)$^{33}$-OH with the following series of Fmoc-protected amino acids: His(Trt)$^{32}$-OH, Leu$^{31}$-OH, (Boc)Lys$^{30}$-OH, Aib$^{29}$-OH, Leu$^{28}$-OH, Leu$^{27}$-OH, (Boc)Lys$^{26}$-OH, (OtBu)Glu$^{25}$-OH, Leu$^{24}$-OH, Leu$^{23}$-OH, (OtBu)Glu$^{22}$-OH, (Pbf)Arg$^{21}$-OH, (Pbf)-Arg$^{20}$-OH, (Pbf)Arg$^{19}$-OH, Leu$^{18}$-OH, and (OtBu)Asp$^{17}$-OH.

16. The process of claim 15, wherein the coupling reagent comprises PyBOP, HOBt, DIC, and DIEA.

17. The process of claim 15, wherein the amine base is piperidine.

18. The process of claim 17, wherein the piperidine is present as an approximately 20% solution by volume in DMF.

19. The process of claim 15, wherein each coupling step is performed using from about 1.05 to about 2 molar equivalents of Fmoc-amino acid, relative to the bound peptide.

20. The process of claim 15, wherein performing the recoupling reaction comprises performing a coupling reaction with the Fmoc-protected amino acid one or more additional times, using from 0.15 to 1.5 molar equivalents of the respective Fmoc-amino acid relative to the bound peptide, and repeating said coupling until a negative Kaiser or Chloranil test result is obtained.

21. A process for the preparation of abaloparatide comprising:

a) anchoring Fmoc-protected alanine (Fmoc-Ala$^{34}$-OH) to Rink amide 4-methylbenzhydrylamine (MBHA) resin;

b) capping the resin obtained in step a) by acetylation;

c) selectively cleaving the Fmoc group with a solution comprising piperidine to provide an N-terminus;

d) coupling a carboxyl terminus of Fmoc-Thr(tBu)$^{33}$-OH to the N-terminus in the presence of a coupling reagent comprising benzotriazol-1-yloxytripyrrolidinophosphonium hexafluorophosphate (PyBOP), 1-Hydroxybenzotriazole (HOBt), N,N'-diisopropylcarbodiimide (DIC), and diisopropylethylamine (DIEA), performing a Kaiser and/or Chloranil test after each step d) to confirm complete incorporation of each Fmoc-protected amino acid, and repeating said step d) if a positive Kaiser or Chloranil test result is obtained;

e) selectively cleaving the Fmoc group with a solution comprising piperidine to provide an N-terminus;

f) repeating steps d) and e) sequentially, replacing the Fmoc-Thr(tBu)$^{33}$-OH with the following series of Fmoc-protected amino acids: His(Trt)$^{32}$-OH, Leu$^{31}$-OH, (Boc)Lys$^{30}$-OH, Aib$^{29}$-OH, Leu$^{28}$-OH, Leu$^{27}$-OH, (Boc)Lys$^{26}$-OH, (OtBu)Glu$^{25}$-OH, Leu$^{24}$-OH, Leu$^{23}$-OH, (OtBu)Glu$^{22}$-OH, (Pbf)Arg$^{21}$-OH, (Pbf)-Arg$^{20}$-OH, (Pbf)Arg$^{19}$-OH, Leu$^{18}$-OH, and (OtBu)Asp$^{17}$-OH, and performing a Kaiser and/or Chloranil test after each step d) before each step e) to confirm complete incorporation of each Fmoc-protected amino acid, and repeating said step d) if a positive Kaiser or Chloranil test result is obtained;

g) coupling a carboxyl terminus of Fmoc-(Trt)Gln$^{16}$-OH to the N-terminus, wherein coupling comprises adding to a suspension of the bound peptide in dimethylformamide from about 1.05 to about 2 molar equivalents of Fmoc-(Trt)Gln$^{16}$-OH, relative to the bound peptide, in the presence of a coupling reagent comprising PyBOP, HOBt, DIC, and DIEA, and allowing the mixture to react for a period of time;

h) adding to the mixture a further from about 1.05 to about 2 molar equivalents of Fmoc-(Trt)Gln$^{16}$-OH, relative to the bound peptide, in the presence of additional PyBOP, HOBt, DIC, and DIEA;

i) selectively cleaving the Fmoc group with a solution comprising piperidine to provide an N-terminus;

j) coupling a carboxyl terminus of Fmoc-Ile$^{15}$-OH to the N-terminus in the presence of a coupling reagent comprising PyBOP, HOBt, DIC, and DIEA;

k) selectively cleaving the Fmoc group with a solution comprising piperidine to provide an N-terminus;

l) repeating steps j) and k) sequentially, replacing Fmoc-Ile$^{15}$-OH with the following series of Fmoc-protected amino acids: Ser (tBu)$^{14}$-OH, Lys (Boc)$^{13}$-OH, Gly$^{21}$-OH, Lys(Boc)$^{11}$-OH, Asp(OtBu)$^{10}$-OH, His(Trt)$^{9}$-OH, Leu$^{8}$-OH, Leu7-OH, Gln(Trt)$^{6}$-OH, His (Trt)$^{5}$-OH, Glu (OtBu)$^{4}$-OH, Ser(tBu)$^{3}$-OH, Val$^{2}$-OH, and Ala$^{1}$-OH;

m) performing a Kaiser and/or Chloranil test after each step j) before each step k) to confirm complete incorporation of each Fmoc-protected amino acid, and repeating said step j) if a positive Kaiser or Chloranil test result is obtained; and n) treating the resulting anchored, protected abaloparatide with a solution comprising trifluoroacetic acid to provide crude abaloparatide.

22. The process of claim 21, wherein:

each initial coupling reaction is performed using from about 1.05 to about 2 molar equivalents of the respective Fmoc-amino acid relative to the bound peptide; and any repeated couplings performed following a positive Kaiser or Chloranil test are performed using from 0.15 to 2 molar equivalents of the respective Fmoc-amino acid.

23. The process of claim 21, wherein in step f), the coupling of Fmoc-protected Aib$^{29}$-OH is repeated once prior to cleavage of the Fmoc group, without regard to the Kaiser or Chloranil test, the repeated coupling using from about 1.05 to about 2 equivalents of the Fmoc-protected Aib$^{29}$-OH.

24. The process of claim 21, wherein in step f), the coupling of the Fmoc-protected Leu$^{28}$-OH is repeated once prior to cleavage of the Fmoc group, without regard to the Kaiser or Chloranil test, the repeated coupling using from about 1.05 to about 2 equivalents of the Fmoc-protected Leu$^{28}$-OH.

25. The process of claim 21, wherein the piperidine is present as an approximately 20% solution by volume in DMF.

26. The process of claim 21, wherein the obtained crude abaloparatide contains less than about 1% of des-Gln$^{16}$-abaloparatide by weight, based on the total weight of the crude abaloparatide.

27. The process of claim 21, wherein the obtained crude abaloparatide contains less than about 0.5% des-Gln$^{16}$-abaloparatide by weight, based on the total weight of the crude abaloparatide.

28. The process of claim 21, wherein the obtained crude abaloparatide contains less than about 0.3% des-Gln$^{16}$-abaloparatide by weight, based on the total weight of the crude abaloparatide.

\* \* \* \* \*

SEQUENCE LISTING

```
Sequence total quantity: 2
SEQ ID NO: 1            moltype = AA  length = 34
FEATURE                 Location/Qualifiers
source                  1..34
                        mol_type = protein
                        organism = synthetic construct
MOD_RES                 29
                        note = Aib
MOD_RES                 34
                        note = AMIDATION
SEQUENCE: 1
AVSEHQLLHD KGKSIQDLRR RELLEKLLXK LHTA                          34

SEQ ID NO: 2            moltype = AA  length = 18
FEATURE                 Location/Qualifiers
source                  1..18
                        mol_type = protein
                        organism = synthetic construct
MOD_RES                 13
                        note = Aib
MOD_RES                 1
                        note = O-t-Bu
```

```
MOD_RES          3
                 note = 2,2,4,6,7-pentamethyldihydrobenzofuran-5-sulfonyl
MOD_RES          4
                 note = 2,2,4,6,7-pentamethyldihydrobenzofuran-5-sulfonyl
MOD_RES          5
                 note = 2,2,4,6,7-pentamethyldihydrobenzofuran-5-sulfonyl
MOD_RES          6
                 note = O-t-Bu
MOD_RES          9
                 note = -O-t-Bu
MOD_RES          10
                 note = BOC
MOD_RES          14
                 note = BOC
MOD_RES          15
                 note = Trt
MOD_RES          16
                 note = t-Bu
MOD_RES          18
                 note = amidation, Rink amide MBHA resin bound
SEQUENCE: 2
DLRRRELLEK LLXKLHTA                                                   18
```